United States Patent [19]

Litman et al.

[11] Patent Number: 4,756,828
[45] Date of Patent: Jul. 12, 1988

[54] CHROMATOGRAPHIC STRIP HAVING NON-COMPRESSED EDGES

[75] Inventors: David Litman, Los Altos; Robert Zuk, Menlo Park; Gerald Rowley, San Jose, all of Calif.

[73] Assignee: Syntex (U.S.A.) Inc., Palo Alto, Calif.

[21] Appl. No.: 599,386

[22] Filed: Apr. 12, 1984

[51] Int. Cl.$^4$ ............................................. G01N 33/53
[52] U.S. Cl. ........................................ 435/7; 162/194; 162/260; 162/286; 210/198.2; 210/456; 219/121.67; 219/121.72; 219/121.74; 219/121.8; 422/56; 422/70; 422/71; 427/3; 435/803; 435/805; 436/528; 436/161; 436/162; 436/810
[58] Field of Search ............................ 435/7, 803, 805; 436/528, 161, 162, 169, 810, 824; 422/56, 70, 71; 210/456, 198.2; 162/194, 286, 260; 427/3; 219/121 LG, 121 LN, 121 LQ, 121 LW

[56] References Cited

U.S. PATENT DOCUMENTS 4,235,601  11/1980  Deutsch et al. ..................... 436/810
4,430,548   2/1984  Macken ......................... 219/121 LG
4,435,504   3/1984  Zuk et al. ................................ 435/7

*Primary Examiner*—Christine M. Nucker
*Attorney, Agent, or Firm*—Theodore J. Leitereg; Carole F. Barrett

[57] ABSTRACT

A device is disclosed for use in a chromatographic system wherein a component of a mixture is partitioned between a liquid phase and an immobile phase. The device comprises at least one strip of a bibulous material. In the chromatographic system the component traverses at least a portion of the strip. The strip generally has a longitudinal edge substantially corresponding to the direction of traverse of the component. The longitudinal edge has the characteristic of substantially the same rate of traversal by the component along this edge when compared to the rate of traversal of the component along the body of the strip. The strips are prepared from a sheet of a bibulous material by non-deformative or non-compressive cutting of the sheet. The preferred cutting means is a laser beam.

21 Claims, 1 Drawing Sheet

CHROMATOGRAPHIC STRIP HAVING NON-COMPRESSED EDGES

BACKGROUND OF THE INVENTION

1. Field of the Invention

This invention relates to improved chromatographic strips and methods of preparing them. The improved chromatographic strips of the invention are useful in analytical chromatography, particularly as immunochromatographic strips.

A number of materials are known for use as chromatographic strips. Generally, the material is "bibulous" or "porous," comprising a random or oriented pile of fibers such as found, for example, in cellulose, fiberglass, woven cloth, cotton, polyester, etc., and the like. The preferred material is paper, which is a random pile of cellulose fibers. The tortuous interstitial and interconnected capillaries of such a random pile of fibers create both a drive for and a resistance to a mobile phase, which, in a chromatographic system, traverses at least a portion of the strip. The mobile phase is generally a liquid medium, most usually a solvent. The transfer of the mobile phase to channels within the random pile, which channels have ever smaller diameters, provides the free energy gradient to drive the mobile phase through the medium. Dead end pores trap the mobile phase and limit its traversal of the chromatographic strip.

The chromatographic strips are normally prepared from larger sheets from which they are cut by mechanical means. The most widely used form of mechanical cutting involves a blade or wire.

Mechanical cutting of the sheet into strips results in a deformation of the edge of the strip along the cutting line. This deformation takes the form of a compression of the edges of the strip. The fibers which form the strip, when cut mechanically, are pushed closer together at the cut edges when compared to the distance between the fibers in the body of the strip. This deformation of the edges of the strip frequently results in a faster rate of traversal for the liquid medium at the edges of the strip than through the body of the strip. The fronts of components traversing the strip become concave rather than flat.

In many situations employing a chromatographic strip it is important that the shape of the front of the traversing component be flat. In analytical and preparative chromatography, it is usually preferable to have a flat front. An example of such a situation is affinity chromatography. In such a test antibodies are attached to a porous insoluble support. During migration of an antigen-containing solution on the porous support, the migration of the antigen solute is specifically delayed in comparison to the migration of the solvent and other solutes. The relative delay decreases with increasing antigen concentration. Accurate quantitations of the concentration of analyte in a sample to be analyzed requires that the position of the analyte front relative to the solvent front be measured accurately. The position of a flat front can usually be measured with greater precision and accuracy than that of a concave front, and a higher degree of accuracy is thereby obtained in a chromatographic assay. Moreover, in preparative chromatography a linear front permits more ready separation and isolation of the pure component.

2. Brief Description of the Prior Art

U.S. Pat. No. 4,168,146 describes an immunoassay employing immunochromatography with antigens followed by contacting the immunochromatograph with an aqueous solution containing labelled antibodies. An enzyme chromatographic immunoassay is described in U.S. Ser. No. 398,505, filed July 15, 1982, now U.S. Pat. No. 4,435,504.

SUMMARY OF THE INVENTION

A device is disclosed for use in a chromatographic system wherein a component of a mixture is partitioned between a liquid phase and an immobile phase. The device comprises at least one strip of a bibulous material. In the chromatographic system the component in a mobile phase, usually in a liquid medium, traverses at least a portion of the strip. The strip has a longitudinal edge that comes in contact with the traversing component during the chromatographic process and that lies in a direction substantially corresponding to the direction of traverse of the component. The longitudinal edge has the characteristic of substantially the same rate of traversal of the component along this edge when compared to the rate of traversal of the component along the body of the strip. The longitudinal edge has substantially the same degree of deformation as the body of the strip. Thus, the present device has the characteristic that the front of the traversing component remains substantially flat over the traversed portion of the strip. The device of the invention is prepared by a non-compressive or non-deformative cutting of a sheet of bibulous material into strips. Such non-compressive cutting may be achieved, for example, by cutting the sheet of bibulous material with a laser beam.

DESCRIPTION OF THE SPECIFIC EMBODIMENTS

Figure 1:
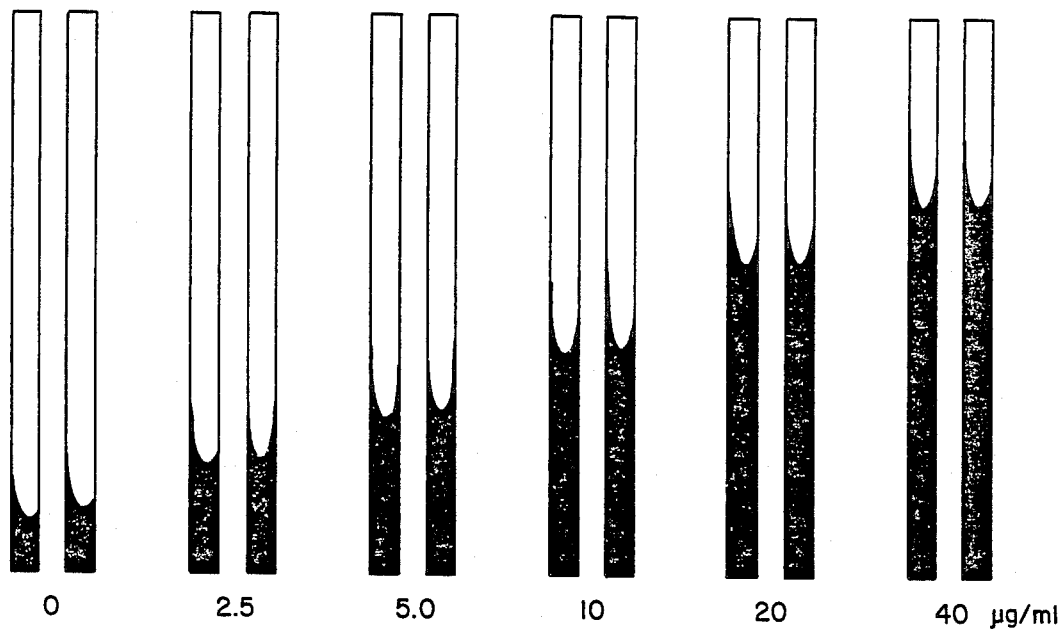
FIG. 1 is a depiction of immunochromatographic strips prepared by mechanical cutting of the prior art, which strips have been utilized in an immunochromatography.

The benefits of the present invention may be achieved by cutting a sheet of bibulous material into chromatographic strips employing means that do not compress (non-compressive) or deform (non-deformative) the longitudinal side edge of said strip. By the term "non-compressive" or "non-deformative" is meant that the cutting does not substantially distort the cut edges of the strip when compared to the body of the strip or when compared to edges cut by compressive cutting means. That is, the relationship of the pores within the bibulous material is substantially the same near the cut edge as it is in the body of the strip. The pores are not compressed near the cut edge as the pores are near the edge cut by compressive cutting means.

The preferred means for achieving non-deformative or non-compressive cutting of a sheet of bibulous material to produce chromatographic strips in accordance with the present invention is a laser beam. Laser cutting devices are well known in the art.

The parameters for cutting the sheets, such as intensity of the laser beam, the speed of cutting, and the like will be interdependent and will also depend on the nature of the bibulous material, the thickness of the bibulous material, the ultimate use of the chromatographic strips, and so forth. In general, the cutting parameters will be sufficient to cut the sheet of bibulous material but insufficient to produce significant deformation or compression of the cut edges which would result in accelerated traversal of the liquid medium along the side edge of the strip when compared to the rate of traversal of the liquid medium along the body of the strip or when compared to the rate of traversal along an edge cut by compressive means.

The following are parameters for cutting paper having a thickness from about 0.05 to 2 mm, which parameters are provided by way of example and not limitation.

The energy of the laser beam will be from about 5 to 350 watts CW (continuous wave), preferably from about 50 to 100 watts CW. The cutting speed will depend upon the intensity of the laser beam and should be adjusted, where appropriate, to minimize discoloration of the bibulous material. The cutting speed is adjusted to maintain optimal cut edge quality. At an intensity of the laser beam of about 50 watts CW the cutting speed generally will be from about 5-50 centimeters per second, preferably from about 20-25 centimeters per second. The particular energy and cutting speed to be employed in a specific situation may be easily determined by those skilled in the art keeping in mind the above teaching.

Where discoloration of the chromatographic material might occur during the laser cutting operations, an air pressure stream may be focused on the area of the sheet being cut. In general, the pressure of the air stream should be sufficient to reduce any discoloration of the chromatographic material and should not interfere with the cutting operation. The pressure may vary from about 20 to 100 psig, preferably from about 50 to 70 psig.

The non-deformative cutting method of the present invention may be applied to all types of bibulous materials which find use in chromatographic systems. Chromatographic material means a material susceptible to traversal by a mobile material, either a solvent or a solute (traversing component) in response to capillary force, gravitational force, electrostatic force, positive pressure, or the like. Such materials include inorganic powders such as silica, magnesium sulfate, and alumina: natural polymeric materials, particularly cellulosic materials, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, etc.; either used by themselves or in conjunction with other materials; ion exchange resins; ceramic materials; and the like.

The chromatographic strips are generally prepared from sheets of uniform thickness of the bibulous material. The strips may have a variety of thicknesses, usually from 0.05 to 2 mm, preferably 0.1 to 0.5 mm, and may vary in shape usually being rectangular, square, oval, or circular, preferably rectangular. The particular dimensions and shape will be determined by the chromatographic method in which the strips will be employed, normally having a maximum width, perpendicular to the flow, of less than 30 cm and a maximum length, parallel to the flow, less than 40 cm; more frequently a maximum width of 2 cm and a maximum length of 15 cm, preferably a maximum width of 1 cm and a maximum length of 10 cm. All that is required in the present invention is that the strip have at least one longitudinal edge generally corresponding to the direction of flow of the traversing component. Longitudinal edge intends a border of the chromatographic material and is the boundary where the material begins or ends. The structure of the bibulous material may be varied widely and includes fine, medium fine, medium, medium coarse and coarse. The surface may be varied widely with varying combinations of smoothness and roughness combined with hardness and softness. The chromatographic strip may be used independently or it may be supported by a variety of inert supports. Exemplary of such supports are Mylar ®, polystyrene, polyethylene, or the like.

Chromatographic strips prepared in accordance with the teaching contained herein find particular use in affinity chromatography, for example, immunochromatography. Immunochromatographic methods comprise any number of different specific embodiments. The general characteristics of an immunochromatographic method are that an antigen or antibody is immobilized on the chromatographic material and the complementary binding partner, antibody or antigen, in a liquid medium traverses a portion of a strip of the bibulous material.

Exemplary of an immunochromatographic method is the immunoassay disclosed in U.S. Pat. No. 4,168,146 (herein incorporated by reference in its entirety). The disclosed method is based on utilizing strips of a porous carrier material having antibodies bound to it. In the method a portion of each of the strips is contacted with an aqueous sample containing the antigen to be quantified. Capillary migration is allowed to take place. The antigen-containing area of the strip is detected by wetting it with antibodies in an aqueous vehicle. The antibodies are normally bound to a signal producing system such as, for example, a water soluble fluorescent color indicating compound or to an enzyme that catalyzes a color-developing reaction.

Another immunochromatographic method is disclosed in U.S. patent application Ser. No. 398,505, filed July 15, 1982, now U.S. Pat. No. 4,435,504 (herein incorporated by reference in its entirety). The disclosed method allows detection of an analyte in a sample where a quantitative determination may be readily made without special equipment. The sample is immunochromatographed on a bibulous carrier to which is conjugated a specific binding partner for the analyte. The immunochromatography may be conducted in the presence or absence of a labeled conjugate. The label is a member of an enzymatic signal producing system, which includes one or more enzymes. After chromatographing the samples, if the labeled conjugate was not included in the sample, the chromatograph is contacted with a labeled specific binding pair member which binds to the chromatograph in relation to the distance travelled by the analyte in the sample. By providing appropriate reagents to produce a detectable signal, e.g., two enzymes where the substrate of one enzyme is the product of another enzyme, a final product is produced which provides for a detectable signal. In such a case the distance travelled by the analyte may be defined, which distance is related to the amount of analyte in the sample.

The present invention, therefore, comprises a diagnostic device for use in immunoassays. The diagnostic device comprises a bibulous material providing liquid travel through capillarity and at least one non-diffusively bound member of a specific binding pair ("mip"). The device may also include one or more members of a signal producing system. Generally, the analyte to be measured is a mip selected from the group consisting of ligand and receptor. The ligand and receptor are related in that the receptor specifically binds to a polar and spacial organization of the ligand, being able to distinguish the ligand from other compounds having similar characteristics. The signal producing system member, for example, may be an enzyme or a fluorescent compound. Generally, the immunochromatographic strip contains a plurality of mips attached thereto. The thickness of the immunochromatographic strip will generally vary from about 0.05 mm to about 2 mm, more usually being about 0.1 mm to 0.5 mm, preferably from about 0.2 mm to about 0.4 mm. Usually, the strip will have a width of from about 2 to 12 mm, preferably from about 3 to 8 mm, and will have a length of from about 20 to 250 mm, preferably from about 30 to 150 mm.

Methods for binding a wide variety of materials to a bibulous support are found in the literature. See for example, U.S. Pat. No. 4,168,146. The amount of a mip which is bound to the bibulous material will vary depending upon the size of the immunochromatographic strip and the amount required to bind the homologous mip. Generally, the amount of mip will range from about $10^{-5}$ to $10^{-15}$ moles per square centimeter, more usually from about $10^{-7}$ to $10^{-12}$ moles per square centimeter. The number of moles per unit area will be varied in order to insure that there is sufficient modification of the distance traversed by the traversing component along the affinity chromatographic strip within the concentration range of interest.

Also included within the scope of the present invention are diagnostic kits which comprise (1) at least one chromatographic strip prepared in accordance with the present invention to which is attached a member of a specific binding pair, (2) a member of the specific binding pair conjugated to a member of a signal producing system, and (3) any other members of the signal producing system as well as any buffers or the like for conducting an affinity chromatographic assay.

The following examples are offered by way of illustration and not by way of limitation.

The following abbreviations are used hereafter: HRP—horse radish peroxidase; NHS—N-hydroxy succinimide; EDAC—ethyl dimethylaminopropyl carbodiimide; DMF—dimethyl formamide; BSA—bovine serum albumin. Temperatures not otherwise indicated are Celsius, while parts are by weight except for mixtures of liquids which are by volume.

EXAMPLE 1

Preparation of Immunochromatographic Sheets

A sheet of Whatman 31 ET of about 550 cm² was immersed in 1.8 l. $CH_2Cl_2$, 0.2M in carbonyldiimidazole, and the mixture gently stirred for one hour at room temperature. Additional sheets were activated in the same activating solution. Each sheet was then washed with 300 ml $CH_2Cl_2$ and air dried with an air gun over about 20 sec. The sheet was then immersed in a solution of 500 μl of a 49 mg/ml solution of antitheophylline and 200 ml of buffer 0.1M sodium phosphate, pH 7.0, 0.2M NaCl; and the mixture was mildly shaken for 4 hours at room temperature. After washing with the phosphate buffer, the solution was then immersed in 4% aqueous Dextran T10 solution to serve as a preservative, followed by blotting the sheet, freezing and lyophilizing.

EXAMPLE 2

Preparation of Immunochromatographic Strips

A Coherent Model 42, $CO_2$ laser at 50 watts CW (from Coherent, Inc., Palo Alto) and Anomatic II CNC X-Y table were employed. A Coherent Model 303 coaxial gas jet was used at an air pressure of 60 psig. A standard cutting box was used.

The cutting box was placed on the X-Y table and a sheet of plexiglass was placed on the cutting box. A narrow slot was cut in the plexiglass using the laser beam. An immunochromatographic sheet prepared in Example 2 was placed over the plexiglass. The sheet was cut into strips which were 4.5 mm wide and 90 mm in length. Cutting speeds of 19 and 26 centimeters per second were employed. The performance of the immunochromatographic strips cut at the two different speeds was substantially identical.

EXAMPLE 3

Preparation of HRP-Oxyamine

To 5 ml of 10 mg/ml horse radish peroxidase in 5 mM sodium acetate, pH 4.5 buffer, was added 50 μl 0.2M sodium periodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° C. and 2.9 ml of 0.2M 2,2'-oxy-bis-ethylamine in 0.5M carbonate buffer, pH 9.5, at 4° added. The pH of the mixture was adjusted to 9.5 with 1N sodium hydroxide, stirred for 2 hrs and 3.52 ml of a 4 mg/ml sodium borohydride-water solution added and the mixture allowed to react for 3 hr, followed by chromatography through a Sephadex G-50 column.

The above procedure was repeated using 400 mg of HRP and 3.5 g of 2,2'-oxy-bis-ethylamine. No significant change in enzyme activity was observed between the native amine and the modified amine, which has about four additional amino groups.

EXAMPLE 4

Conjugation of Theophylline and HRP

Into a reaction flask was introduced 8.1 mg of 1-methyl-3-(3'-carboxypropyl)xanthine, 3.8 mg of NHS, 6.7 mg EDAC and 125 μl DMF and the mixture allowed to stand overnight at room temperature.

To four 1.3 ml samples of HRP-oxyamine (1 mg) from Example 3 in 0.1M sodium carbonate, pH 9.0 was added varying amounts of the ester prepared above to provide for preparations having mole ratios of theophylline to HRP of 400; 200, and two of 100 each. Into the first reaction mixture (400 mole ratio) was added 0.217 ml of DMF and 66 μl of the above ester in 8.25 μl increments over a period of about 2 hrs. Into the second reaction mixture (200 mole ratio), 0.238 ml of DMF was added and 33 μl of the ester added incrementally in 8.25 μl increments. Into the third reaction mixture (100 mole ratio), 0.24 ml of DMF was added and 16.5 μl of the ester added in 8.2 μl increments, while in the final reaction mixture (100 mole ratio), no DMF was added, and 8.25 μl of the ester was added in 2.1 μl increments. During the addition, the temperature was maintained at 4°, and the mixture then allowed to stand overnight at 4°.

The reaction mixtures were then worked up by chromatography on G-25 Sephadex ® with standard buffer. Folin and UV spectroscopic analysis indicated theophylline/HRP ratios of 6.9, 4.0, 1.6 and 2.1, respectively.

EXAMPLE 5

Immunochromatographic Assay

In carrying out the assay, the strips prepared in Example 2 were employed. Samples containing 0, 2.5, 5.0, 10, 20 and 40 μg/ml (10 μl) were mixed with 0.5 ml of a solution containing 0.1M $NaH_2PO_4$, 0.2M NaCl, pH 7.0, 1 mg/ml BSA, 0.05% Triton QS-15, 100 μg/ml glucose oxidase (Sigma, E.C. 1.1.3.4), and 0.2 μg/ml HRP-theophylline conjugate. The end of a strip was dipped into this mixture. After the solution had reached the top of the strip by capillary migration (6–12 min), the strip was removed from the enzyme solution and totally immersed in a development solution comprising 15 ml of 50 mM glucose and 200 μg/ml of 4-chloro-1-naphthol and allowed to stand for 20 min. The results are depicted in FIG. 2.

For purposes of comparison assays were also conducted employing immunochromatographic strips prepared from the sheet of Example 2 by cutting the sheets on a slitter. Referring to FIG. 1 it can be seen that the slitter cut strips exhibit extensive concavity of the front resulting from accelerated traversal of the liquid sample along the longitudinal edges of the strip when compared to the rate of traversal of the liquid sample along the body of the strip.

Figure 2:
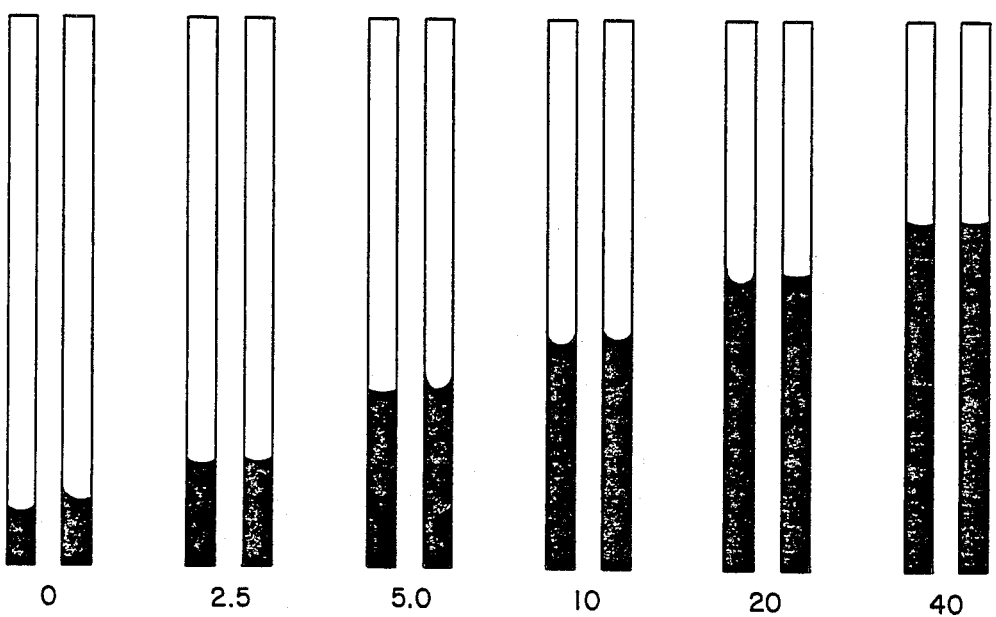
FIG. 2 is a depiction of immunochromatographic strips prepared in accordance with the present invention, which strips have been utilized in an immunochromatography.

FIG. 2 demonstrates that the accelerated traversal of the liquid sample along the longitudinal edges of the strips cut in accordance with the invention has been minimized when compared to the rate of traversal of the liquid sample along longitudinal edges of strips cut using a slitter.

What is claimed is:

1. A device for use in a chromatographic system wherein a component of a mixture is partitioned between a liquid phase and an immobile phase, said device comprising at least one chromatographic strip consisting essentially of a bibulous material, wherein in said system said liquid phase forms a front traversing at least a portion of said strip, said strip having a body and at least one longitudinal edge comprising a border of said strip and lying in a direction substantially corresponding to the direction of traverse of said liquid phase wherein the longitudinal edge of said strip has the characteristic of substantially the same rate of traversal of said liquid phase along said longitudinal edge when compared to the traversal of said liquid phase along the body of said strip such that the front of the traversing liquid phase is substantially flat.

2. A paper chromatographic strip having a substantially non-compressed longitudinal edge.

3. An immunochromatographic device comprising the strip of claim 2 to which a member of a specific binding pair is non-diffusively bound.

4. The device of claim 3 wherein the member of the specific binding pair is an antigen or an antibody.

5. The device of claim 3 wherein a member of a signal producing system is bound to said strip.

6. The immunochromatographic device of claim 5 wherein the member of a signal producing system is an enzyme.

7. The immunochromatographic device of claim 5 wherein the signal producing system comprises two enzymes which are related by the product of one enzyme being a substrate for the other enzyme.

8. A device for use in a chromatographic system wherein a component of a mixture is partitioned between a liquid phase and an immobile phase, said device comprising at least one chromatographic strip cut from a sheet consisting essentially of a bibulous material, wherein in said system said liquid phase forms a front traversing at least a portion of said strip, said strip having a body and at least one longitudinal edge comprising a border of said strip and lying in a direction substantially corresponding to the direction of traverse of said liquid phase wherein the cut longitudinal edge of said strip has the characteristic that the relationship of pores within the bibulous material is substantially the same near the cut longitudinal edge as the relationship of the pores in the body of said strip such that the front of the traversing liquid phase is substantially flat.

9. An immunochromatographic device comprising the strip of claim 8 to which a member of a specific binding pair is non-diffusively bound.

10. The device of claim 9 wherein the member of the specific binding pair is an antigen or an antibody.

11. The device of claim 9 wherein a member of a signal producing system is bound to said strip.

12. The immunochromatographic device of claim 11 wherein the member of a signal producing system is an enzyme.

13. The immunochromatographic device of claim 11 wherein the signal producing system comprises two enzymes which are related by the product of one enzyme being a substrate for the other enzyme.

14. The device of claim 8 wherein said strip is cut from a sheet of said porous material by non-compressive cutting means.

15. The strip of claim 14 wherein said non-compressive cutting means is a laser beam.

16. In a paper chromatographic strip having a body and two longitudinal side edges, the improvement which comprises said longitudinal edges having substantially the same degree of compression as the body of said strip.

17. In an immunochromatographic method, the improvement which comprises employing a paper chromatographic strip having a substantially non-compressed longitudinal edge.

18. In an immunochromatographic method, the improvement which comprises employing an immunochromatographic device comprising the strip of claim 17 to which a member of a specific binding pair is non-diffusively bound.

19. In an immunochromatographic method, the improvement which comprises employing a device wherein a component of a mixture is partitioned between a liquid phase and an immobile phase, said device comprising at least one strip cut from a sheet consisting essentially of a bibulous material wherein said liquid phase forms a front traversing at least a portion of said strip wherein the strip has a body and at least one longitudinal edge comprising a border of said strip and lying in a direction substantially corresponding to the direction of traverse of said liquid phase in said system wherein the longitudinal edge of said strip has the characteristic of substantially the same rate of traversal of said component along said longitudinal edge when compared to the traversal of said liquid phase along the body of the strip such that the front of the traversing liquid phase remains substantially flat over the traversed portion of the strip, and wherein a member of a specific binding pair and an enzyme are non-diffusively bound to said strip.

20. In an immunochromatographic method, the improvement which comprises employing a chromatographic strip having a body and two longitudinal cut edges having substantially the same degree of compression as the body of the strip.

21. A diagnostic kit, which comprises in packaged combination
   (a) the device of claim 3, and
   (b) a member of said specific binding pair bound to a member of a signal producing system.

* * * * *